(12) United States Patent
Takemura et al.

(10) Patent No.: US 11,858,920 B2
(45) Date of Patent: Jan. 2, 2024

(54) EPISULFIDE COMPOUND AND COMPOSITION FOR OPTICAL MATERIAL

(71) Applicant: MITSUBISHI GAS CHEMICAL COMPANY, INC., Tokyo (JP)

(72) Inventors: Kouhei Takemura, Tokyo (JP); Yousuke Imagawa, Tokyo (JP); Hiroshi Horikoshi, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 597 days.

(21) Appl. No.: 17/261,303

(22) PCT Filed: Jun. 27, 2019

(86) PCT No.: PCT/JP2019/025539
§ 371 (c)(1),
(2) Date: Jan. 19, 2021

(87) PCT Pub. No.: WO2020/021953
PCT Pub. Date: Jan. 30, 2020

(65) Prior Publication Data
US 2021/0340129 A1 Nov. 4, 2021

(30) Foreign Application Priority Data
Jul. 24, 2018 (JP) .................. 2018-138712

(51) Int. Cl.
| | |
|---|---|
| *C08L 81/02* | (2006.01) |
| *C08G 75/08* | (2006.01) |
| *C08K 3/06* | (2006.01) |
| *G02B 1/04* | (2006.01) |
| *C07D 331/02* | (2006.01) |
| *C07D 409/14* | (2006.01) |

(52) U.S. Cl.
CPC ......... *C07D 409/14* (2013.01); *C07D 331/02* (2013.01); *C08G 75/08* (2013.01); *G02B 1/041* (2013.01)

(58) Field of Classification Search
CPC ... C08L 81/02; C08L 2201/10; C07D 331/02; C08G 75/08; C08K 3/06; G02B 1/04; G02B 1/041
See application file for complete search history.

(56) References Cited

U.S. PATENT DOCUMENTS

| | | |
|---|---|---|
| 5,807,975 A | 9/1998 | Amagai et al. |
| 6,117,923 A | 9/2000 | Amagai et al. |
| 6,472,495 B1 | 10/2002 | Yoshimura et al. |
| 2003/0139486 A1 | 7/2003 | Yamada et al. |
| 2004/0122201 A1 | 6/2004 | Yoshimura et al. |
| 2008/0206668 A1* | 8/2008 | Hoshino ............ G03F 7/038 430/322 |
| 2015/0166720 A1 | 6/2015 | Okada et al. |
| 2016/0259091 A1 | 9/2016 | Horita et al. |
| 2018/0127549 A1 | 5/2018 | Imagawa et al. |
| 2018/0265638 A1 | 9/2018 | Namiki et al. |

FOREIGN PATENT DOCUMENTS

| | | |
|---|---|---|
| EP | 0 980 696 A1 | 2/2000 |
| JP | 9-71580 A | 3/1997 |
| JP | 9-110979 A | 4/1997 |
| JP | 9-255781 A | 9/1997 |
| JP | 10-298287 A | 11/1998 |
| JP | 2001-2783 A | 1/2001 |
| JP | 2001-131257 A | 5/2001 |

(Continued)

OTHER PUBLICATIONS

Extended European Search Report issued in European Patent Application No. 19841912.9 dated Sep. 15, 2021.
International Search Report issued in International Patent Application No. PCT/JP2019/025539, dated Sep. 17, 2019 and English Translation thereof.

(Continued)

*Primary Examiner* — Shane Fang
(74) *Attorney, Agent, or Firm* — GREENBLUM & BERNSTEIN, P.L.C.

(57) ABSTRACT

Provided is a composition for optical materials that gives optical materials which can have at least one improved property selected from among satisfactory mold releasability after polymerization and curing, unsusceptibility to separation from the mold during polymerization and curing, transparency, and low-level striae. The present invention further provides a compound represented by formula (1). The composition for optical materials comprises the compound represented by formula (1) and a compound represented by formula (2). (In formula (1), $X_1$ and $X_2$ represent O or S, provided that both $X_1$ and $X_2$ are O or that $X_1$ is O and $X_2$ is S.)

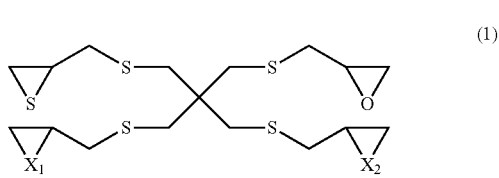

(1)

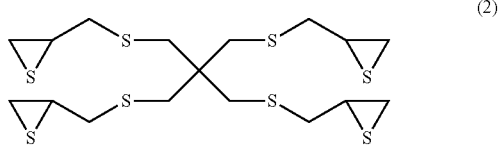

(2)

14 Claims, No Drawings

(56) References Cited

FOREIGN PATENT DOCUMENTS

| JP | 2002-122701 A | 4/2002 |
| JP | 2003-185820 A | 7/2003 |
| WO | 2014/038654 A1 | 3/2014 |
| WO | 2015/098718 A1 | 7/2015 |
| WO | 2016/204080 A1 | 12/2016 |
| WO | 2017/098798 A1 | 6/2017 |

OTHER PUBLICATIONS

Written Opinion of the International Searching Authority issued in International Patent Application No. PCT/JP2019/025539, dated Sep. 17, 2019 and English Translation thereof.

* cited by examiner

EPISULFIDE COMPOUND AND COMPOSITION FOR OPTICAL MATERIAL

TECHNICAL FIELD

The present invention relates to an episulfide compound, which is suitably used for an optical material for a plastic lens, a prism, an optical fiber, an information recording substrate, a filter or the like, in particular for a plastic lens.

BACKGROUND ART

Plastic lenses are lightweight, highly tough and easy to be dyed. Properties particularly required for plastic lenses are: low specific gravity; high transparency; low yellowness; high refractive index and high Abbe number as optical properties; high heat resistance; high strength; and the like. A high refractive index allows a lens to be thinner, and a high Abbe number reduces the chromatic aberration of a lens.

Recently, many organic compounds containing a sulfur atom for providing a high refractive index and a high Abbe number have been reported. Among such compounds, polyepisulfide compounds containing a sulfur atom are known to provide a good balance between the refractive index and the Abbe number (Patent Documents 1-3). Further, since polyepisulfide compounds can be reacted with various compounds, for the purpose of the improvement of physical properties, compositions in combination with various compounds have been proposed (Patent Documents 4-10).

However, in the case of plastic lenses produced from episulfide compounds, there is a case where a lens is broken at the time of demolding due to poor mold releasability, there is a case where required surface accuracy cannot be obtained because a lens is peeled from a mold during polymerization due to an uneven reaction, and there is a case where required characteristics of spectacle lenses in which importance is placed on design property are not sufficiently achieved. Moreover, in the case of compositions containing an episulfide compound, transparency, striae, etc. are deteriorated when the composition is polymerized and cured, and it has been also desired to improve these characteristics.

PRIOR ART DOCUMENTS

Patent Documents

Patent Document 1: Japanese Laid-Open Patent Publication No. H09-110979
Patent Document 2: Japanese Laid-Open Patent Publication No. H09-071580
Patent Document 3: Japanese Laid-Open Patent Publication No. H09-255781
Patent Document 4: Japanese Laid-Open Patent Publication No. H10-298287
Patent Document 5: Japanese Laid-Open Patent Publication No. 2001-002783
Patent Document 6: Japanese Laid-Open Patent Publication No. 2001-131257
Patent Document 7: Japanese Laid-Open Patent Publication No. 2002-122701
Patent Document 8: International Publication WO2014/38654 pamphlet
Patent Document 9: International Publication WO2015/98718 pamphlet
Patent Document 10: International Publication WO2017/098798 pamphlet

SUMMARY OF THE INVENTION

Problems to be Solved by the Invention

Under the above-described circumstances, it is desired to develop an optical material, which can improve at least one of satisfactory mold releasability, peeling prevention property, transparency and low-level striae at the time of polymerization and curing.

One embodiment of the present invention aims to provide an episulfide compound and a composition for optical materials, by which a high-quality optical material having high transparency, low-level striae, etc. is obtained while suppressing reduction in the yield rate caused by mold release failure of a powerful plus lens in which the lens is broken at the time of demolding and peeling defects of a powerful minus lens in which required surface accuracy cannot be obtained because the lens is peeled from a mold at the time of polymerization and curing.

Means for Solving the Problems

Under such circumstances, the present inventors diligently made researches and solved the problem by using a specific episulfide compound and a composition for optical materials containing the episulfide compound, and thus the present invention was achieved.

For example, the present invention is as described below.
[1] An episulfide compound represented by formula (1):

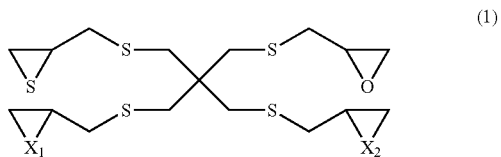

wherein $X_1$ and $X_2$ represent O or S, provided that both $X_1$ and $X_2$ are O or that $X_1$ is O and $X_2$ is S.
[2] A composition for optical materials, which contains an episulfide compound represented by formula (1):

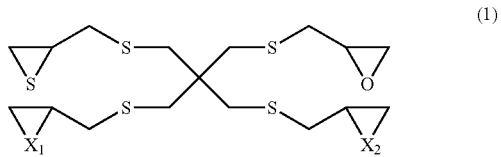

wherein $X_1$ and $X_2$ represent O or S, and an episulfide compound represented by formula (2):

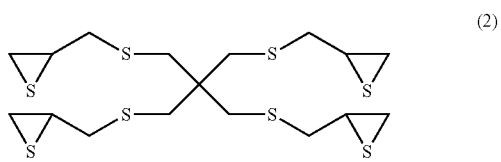

wherein the content of the episulfide compound represented by formula (1) is 0.001 to 5.0% by mass.
[3] The composition for optical materials according to item [2], wherein the content of the episulfide compound represented by formula (2) is 40 to 99.999% by mass.

[4] The composition for optical materials according to item [2] or [3], wherein in the episulfide compound represented by formula (1) contained in the composition for optical materials, the ratio of the total of an episulfide compound (B1) in which both $X_1$ and $X_2$ are O in formula (1) and an episulfide compound (B2) in which $X_1$ is O and $X_2$ is S in formula (1) is 50% by mass or more.

[5] The composition for optical materials according to any one of items [2] to [4], which further contains 1,2,3,5,6-pentathiepane.

[6] The composition for optical materials according to any one of items [2] to [5], which further contains a polythiol.

[7] The composition for optical materials according to any one of items [2] to [6], which further contains sulfur.

[8] A method for producing an optical material, which includes adding a polymerization catalyst to the composition for optical materials according to any one of items [2] to [7] in an amount of 0.0001 to 10% by mass relative to the total amount of the composition for optical materials, followed by polymerization and curing.

[9] An optical material obtained by the method according to item [8].

[10] An optical lens made of the optical material according to item [9].

[11] A method for producing the composition for optical materials according to item [2], which includes a step of reacting an epoxy compound represented by formula (3):

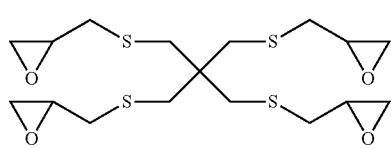

with thiourea and optionally adding the episulfide compound represented by formula (2) thereto to obtain a mixture of the episulfide compound represented by formula (1) and the episulfide compound represented by formula (2).

[12] A method for producing the composition for optical materials according to item [5], which includes: a step of reacting an epoxy compound represented by formula (3):

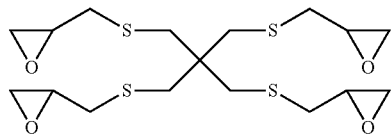

with thiourea and optionally adding the episulfide compound represented by formula (2) thereto to obtain a mixture of the episulfide compound represented by formula (1) and the episulfide compound represented by formula (2); and a step of mixing the mixture with 1,2,3,5,6-pentathiepane.

[13] A method for producing the composition for optical materials according to item [6], which includes: a step of reacting an epoxy compound represented by formula (3):

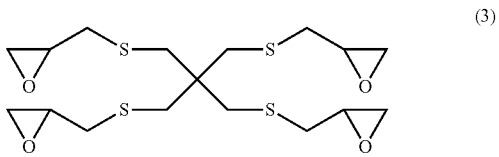

with thiourea and optionally adding the episulfide compound represented by formula (2) thereto to obtain a mixture of the episulfide compound represented by formula (1) and the episulfide compound represented by formula (2); and a step of mixing the mixture with 1,2,3,5,6-pentathiepane and the polythiol.

[14] A method for producing the composition for optical materials according to item [7], which includes: a step of reacting an epoxy compound represented by formula (3):

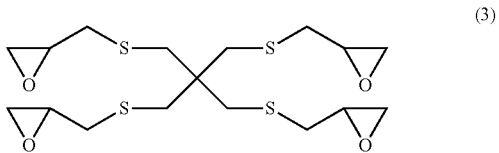

with thiourea and optionally adding the episulfide compound represented by formula (2) thereto to obtain a mixture of the episulfide compound represented by formula (1) and the episulfide compound represented by formula (2); and a step of mixing the mixture, 1,2,3,5,6-pentathiepane, the polythiol and sulfur.

Another embodiment of the present invention is as described below.

[1a] An episulfide compound represented by formula (1):

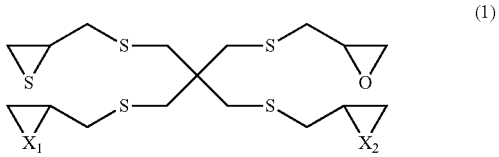

wherein $X_1$ and $X_2$ represent O or S.

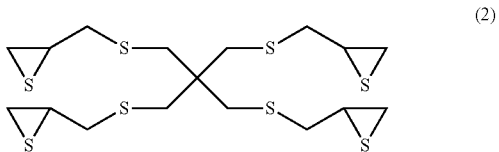

[2a] A composition for optical materials containing the episulfide compound represented by formula (1) according to item [1a] and an episulfide compound represented by formula (2):

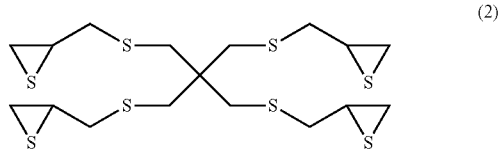

(2)

[3a] The composition for optical materials according to item [2a], wherein the content of the episulfide compound represented by formula (1) according to item [1a] is 0.001 to 5.0% by mass.
[4a] The composition for optical materials according to item [2a] or [3a], wherein the content of the compound represented by formula (2) is 40 to 99.999% by mass.
[5a] The composition for optical materials according to any one of items [2a] to [4a], which further contains 1,2,3,5,6-pentathiepane.
[6a] The composition for optical materials according to any one of items [2a] to [5a], which further contains a polythiol.
[7a] The composition for optical materials according to any one of items [4a] to [6a], which further contains sulfur.
[8a] A method for producing an optical material, wherein a polymerization catalyst is added to the composition for optical materials according to any one of items [2a] to [7a] in an amount of 0.0001 to 10% by mass relative to the total amount of the composition for optical materials, followed by polymerization and curing.
[9a] An optical material obtained by the method according to item [8a].
[10a] An optical lens made of the optical material according to item [9a].
[11a] A method for producing the composition for optical materials according to item [2a], which has a step of reacting an epoxy compound represented by formula (3):

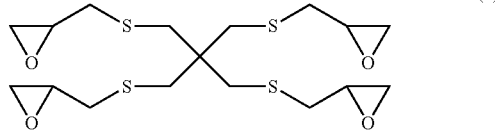

(3)

with thiourea to obtain a mixture of the episulfide compound represented by formula (1) and the episulfide compound represented by formula (2).
[12a] A method for producing the composition for optical materials according to item [5a], which has: a step of reacting an epoxy compound represented by formula (3):

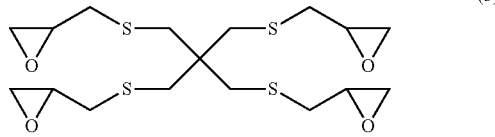

(3)

with thiourea to obtain a mixture of the episulfide compound represented by formula (1) and the episulfide compound represented by formula (2); and a step of mixing the mixture with 1,2,3,5,6-pentathiepane.
[13a] A method for producing the composition for optical materials according to item [6a], which has: a step of reacting an epoxy compound represented by formula (3):

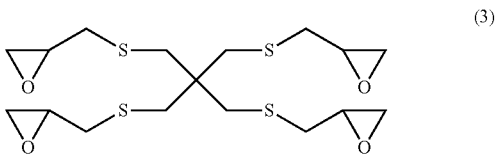

(3)

with thiourea to obtain a mixture of the episulfide compound represented by formula (1) and the episulfide compound represented by formula (2); and a step of mixing the mixture with 1,2,3,5,6-pentathiepane and the polythiol.
[14a] A method for producing the composition for optical materials according to item [7a], which has: a step of reacting an epoxy compound represented by formula (3):

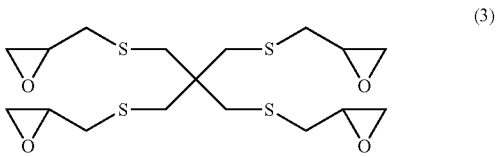

(3)

with thiourea to obtain a mixture of the episulfide compound represented by formula (1) and the episulfide compound represented by formula (2); and a step of mixing the mixture, 1,2,3,5,6-pentathiepane, the polythiol and sulfur.

Advantageous Effect of the Invention

According to the present invention, it is possible to provide an optical material, which can improve at least one of satisfactory mold releasability, peeling prevention property, transparency and low-level striae at the time of polymerization and curing.

According to one embodiment of the present invention, it is possible to provide a composition for optical materials, by which an optical material having excellent quality including transparency and striae is obtained while suppressing reduction in the yield rate caused by mold release failure of a powerful plus lens in which the lens is broken at the time of demolding and peeling defects of a powerful minus lens in which required surface accuracy cannot be obtained because the lens is peeled from a mold.

BEST MODE FOR CARRYING OUT THE INVENTION

Hereinafter, the present invention will be described in detail by way of embodiments, examples, etc., but the present invention is not limited to embodiments, examples, etc. described below and can be arbitrarily changed and then practiced within a range not departing from the gist of the present invention. Note that all the documents and publications cited herein are incorporated herein by reference in their entireties regardless of purposes thereof.

One embodiment of the present invention relates to an episulfide compound represented by formula (1) below (hereinafter also referred to as just "the episulfide compound (1)").

Further, another embodiment of the present invention relates to a composition for optical materials containing the episulfide compound represented by formula (1) below and an episulfide compound represented by formula (2) below (hereinafter also referred to as just "the episulfide compound (2)"), and a composition for optical materials further containing a compound which can be polymerized with the compound represented by formula (2) below, etc. (e.g., a compound (c), a compound (d) and sulfur, which will be described later) according to need.

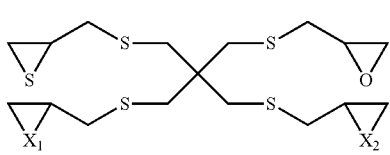

(1)

In formula (1), $X_1$ and $X_2$ represent O (oxygen atom) or S (sulfur atom).

In a specific embodiment, regarding the episulfide compound (1), $X_1$ and $X_2$ are O (i.e., $X_1=X_2=O$), or $X_1$ is O and $X_2$ is S (i.e., $X_1=O$ and $X_2=S$) in formula (1). In one embodiment, $X_1$ and $X_2$ are O (i.e., $X_1=X_2=O$) in formula (1).

When an epoxy ring is contained, rapid polymerization reaction progress is suppressed, and a polymer having excellent transparency, wherein striae are reduced, tends to be obtained thereby.

In one embodiment, the episulfide compound (1) is a mixture of a compound in which $X_1=X_2=O$, a compound in which $X_1=O$ and $X_2=S$ and a compound in which $X_1=X_2=S$, and these compounds may be present at any ratio.

In one embodiment, the episulfide compound (1) includes at least one of a compound in which $X_1=X_2=O$ in formula (1) (hereinafter also referred to as "the episulfide compound (B1)") and a compound in which $X_1=O$ and $X_2=S$ in formula (1) (hereinafter also referred to as "the episulfide compound (B2)"), and according to need, a compound in which $X_1=X_2=S$ in formula (1) (hereinafter also referred to as "the episulfide compound (B3)"). In one embodiment, the episulfide compound (1) includes the episulfide compound (B1) and the episulfide compound (B2). In one embodiment, the episulfide compound (1) includes the episulfide compound (B1), the episulfide compound (B2) and the episulfide compound (B3).

When the episulfide compound (1) is a mixture of the episulfide compound (B1), the episulfide compound (B2) and/or the episulfide compound (B3), the ratio between them is not particularly limited. In one embodiment, the episulfide compound (1) includes 1 to 99% by mass (preferably 5 to 95% by mass, and more preferably 10 to 99% by mass) of the episulfide compound (B1), 1 to 99% by mass (preferably 5 to 95% by mass, and more preferably 10 to 90% by mass) of the episulfide compound (B2) and 0 to 95% by mass (preferably 5 to 95% by mass, and more preferably 10 to 90% by mass) of the episulfide compound (B3) relative to the total mass (100% by mass) of the episulfide compound.

Further, the ratio of the epoxy ring contained in the episulfide compound (1) (the ratio of the number of epoxy rings to the total number of epoxy rings and epithio rings) is preferably 50% or more, more preferably 51% or more, and even more preferably 52% or more.

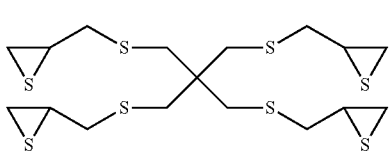

(2)

One embodiment of the present invention is a composition for optical materials containing the episulfide compound represented by formula (1) and the episulfide compound represented by formula (2), and the ratio (content) of the compound represented by formula (1) (the episulfide compound (1)) in the composition for optical materials is preferably 0.001 to 5.0% by mass, more preferably 0.005 to 3.0% by mass, and particularly preferably 0.01 to 1.0% by mass relative to the total amount (100% by mass) of the composition for optical materials. When the content of the compound represented by formula (1) is less than 0.001% by mass, sufficient effects (e.g., high transparency and reduction of striae) may not be obtained, and when the content is more than 5.0% by mass, mold releasability may be deteriorated. Further, in one embodiment of the present invention, the ratio (content) of the compound represented by formula (2) (episulfide compound (2)) in the composition for optical materials is preferably 40 to 99.999% by mass, more preferably 50 to 99.995% by mass, and particularly preferably 60 to 99.99% by mass relative to the total amount (100% by mass) of the composition for optical materials. When the content is 40% by mass or more, excellent optical characteristics of the episulfide compound tend to be obtained.

It is not known exactly why excellent effects as described above (e.g., transparency, low-level striae, peeling prevention property and mold releasability) are obtained by mixing the episulfide compound (1) with the episulfide compound (2), but it is speculated that it is because polymerization reaction progress is moderated.

In one preferred embodiment, in the episulfide compound (1) represented by formula (1) contained in the composition for optical materials, the ratio of the total of the episulfide compound (B1) in which both $X_1$ and $X_2$ are O in formula (1) and the episulfide compound (B2) in which $X_1$ is O and $X_2$ is S in formula (1) is 50% by mass or more (more preferably 60% by mass or more, and even more preferably 70% by mass or more). In one embodiment, in the episulfide compound represented by formula (1) contained in the composition for optical materials, the ratio of the episulfide compound (B1) in which both $X_1$ and $X_2$ are O in formula (1) is 10% by mass or more (more preferably 25% by mass or more, and even more preferably 40% by mass or more).

Hereinafter, the method for producing the compound represented by formula (1) and the compound represented by formula (2) will be described, but the production method is not particularly limited. The compound represented by formula (1) and the compound represented by formula (2) can be obtained by reacting an epoxy compound represented by formula (3) below with thiourea.

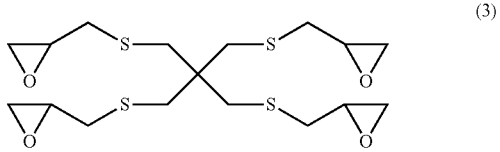
(3)

Note that when obtaining the compound represented by formula (1) by reacting the epoxy compound represented by formula (3) with thiourea, interrupting the reaction before completed is a technique for efficiently obtaining a mixture of the compound represented by formula (1) and the compound represented by formula (2). Specifically, in a mixed solvent of a polar organic solvent which can dissolve thiourea and a non-polar organic solvent which can dissolve the epoxy compound represented by formula (3), the reaction is performed in the presence of an acid or acid anhydride or an ammonium salt, and the reaction is terminated before completed.

That is, in one embodiment, the method for producing the composition for optical materials includes a step of reacting an epoxy compound represented by the above formula (3) with thiourea and optionally adding the episulfide compound represented by formula (2) thereto to obtain a mixture of the episulfide compound represented by formula (1) and the episulfide compound represented by formula (2).

In the case where the composition for optical materials is constituted by using the episulfide compound (1) whose content ratio of the epoxy ring is high (for example, in the case where the episulfide compound (B1) and the episulfide compound (B2) are contained at a high content ratio (for example, the total of B1 and B2 is 50% by mass or more)), usually, after the episulfide compound represented by formula (1) is obtained by reacting the epoxy compound represented by formula (3) with thiourea, the episulfide compound (2) represented by formula (2) is required to be added.

That is, in one embodiment, the method for producing the composition for optical materials includes a step of reacting an epoxy compound represented by the above formula (3) with thiourea and adding the episulfide compound represented by formula (2) thereto to obtain a mixture of the episulfide compound represented by formula (1) and the episulfide compound represented by formula (2).

As the episulfide compound represented by formula (2), a synthesized product obtained by completely reacting the compound of formula (3) with thiourea may be used.

In the method for obtaining the compound represented by formula (1) and the compound represented by formula (2) by means of the aforementioned reaction, thiourea is used in a mole number corresponding to epoxy of the epoxy compound represented by formula (3), i.e., a theoretical amount, but when importance is placed on the reaction rate and the purity, thiourea is used in the theoretical amount to 2.5 times the theoretical amount (mol). The amount is preferably from 1.3 times the theoretical amount (mol) to 2.4 times the theoretical amount (mol), and more preferably from 1.5 times the theoretical amount (mol) to 2.3 times the theoretical amount (mol).

Examples of the polar organic solvent which can dissolve thiourea include: alcohols such as methanol and ethanol; ethers such as diethyl ether, tetrahydrofuran and dioxane; and hydroxy ethers such as methyl cellosolve, ethyl cellosolve and butyl cellosolve. Among them, alcohols are preferred, and methanol is most preferred. Examples of the non-polar organic solvent which can dissolve the epoxy compound represented by formula (3) include: aliphatic hydrocarbons such as pentane, hexane and heptane; aromatic hydrocarbons such as benzene and toluene; and halogenated hydrocarbons such as dichloromethane, chloroform and chlorobenzene. Among them, aromatic hydrocarbons are preferred, and toluene is most preferred. The ratio of the polar organic solvent/the non-polar organic solvent is 0.1 to 10.0 (volume ratio), and preferably 0.2 to 5.0 (volume ratio). When the volume ratio is less than 0.1, thiourea is not sufficiently dissolved and the reaction does not proceed sufficiently, and when the volume ratio is more than 10.0, polymer formation may become pronounced.

The reaction temperature is 10° C. to 30° C. When the reaction temperature is lower than 10° C., not only the reaction rate is reduced, but also thiourea is not sufficiently dissolved and the reaction does not proceed sufficiently, and when the temperature is higher than 30° C., polymer formation becomes pronounced.

Specific examples of the acid or acid anhydride to be used include: inorganic acidic compounds such as nitric acid, hydrochloric acid, perchloric acid, hypochlorous acid, chlorine dioxide, hydrofluoric acid, sulfuric acid, fuming sulfuric acid, sulfuryl chloride, boric acid, arsenic acid, arsenious acid, pyroarsenic acid, phosphoric acid, phosphorous acid, hypophosphoric acid, phosphorus oxychloride, phosphorous oxybromide, phosphorus sulfide, phosphorus trichloride, phosphorus tribromide, phosphorus pentachloride, hydrocyanic acid, chromic acid, nitric anhydride, sulphuric anhydride, boron oxide, arsenic pentoxide, phosphorus pentoxide, chromic anhydride, silica gel, silica alumina, aluminium chloride and zinc chloride; organic carboxylic acids such as formic acid, acetic acid, peracetic acid, thioacetic acid, oxalic acid, tartaric acid, propionic acid, butyric acid, succinic acid, valeric acid, caproic acid, caprylic acid, naphthenic acid, methyl mercaptopropionate, malonic acid, glutaric acid, adipic acid, cyclohexanecarboxylic acid, thiodipropionic acid, dithiodipropionic acid acetic acid, maleic acid, benzoic acid, phenylacetic acid, o-toluic acid, m-toluic acid, p-toluic acid, salicylic acid, 2-methoxybenzoic acid, 3-methoxybenzoic acid, benzoylbenzoic acid, phthalic acid, isophthalic acid, terephthalic acid, salicylic acid, benzilic acid, α-naphthalenecarboxylic acid, β-naphthalenecarboxylic acid, acetic anhydride, propionic anhydride, butyric anhydride, succinic anhydride, maleic anhydride, benzoic anhydride, phthalic anhydride, pyromellitic dianhydride, trimellitic anhydride and trifluoroacetic anhydride; phosphoric acids such as mono-, di- or trimethyl phosphate, mono-, di- or triethyl phosphate, mono-, di- or triisobutyl phosphate, mono-, di- or tributyl phosphate and mono-, di- or trilauryl phosphate, and phosphorous acids in which the phosphate moiety of any of the phosphoric acids is changed to a phosphite; organic phosphorous compounds such as dialkyl phosphorodithioates typified by dimethyl phosphorodithioate; phenols such as phenol, catechol, t-butyl catechol, 2,6-di-t-butyl cresol, 2,6-di-t-butyl ethylphenol, resorcin, hydroquinone, phloroglucin, pyrogallol, cresol, ethyl phenol, butyl phenol, nonyl phenol, hydroxyphenylacetic acid, hydroxyphenylpropionic acid, hydroxyphenylacetamide, methyl hydroxyphenylacetate, ethyl hydroxyphenylacetate, hydroxyphenethyl alcohol, hydroxyphenethyl amine, hydroxybenzaldehyde, phenylphenol, bisphenol A, 2,2'-methylene-bis(4-methyl-6-t-butyl phenol), bisphenol F, bisphenol S, α-naphthol, β-naphthol, aminophenol, chlorophenol and 2,4,6-trichlorophenol; and sulfonic acids such as methanesulfonic acid, ethanesulfonic acid, butanesulfonic acid, dodecanesulfonic acid, benzenesulfonic acid, o-toluenesulfonic acid, m-toluenesulfonic acid, p-toluenesulfonic acid, ethylbenzenesulfonic acid, butylbenzenesulfonic acid, dodecylbenzenesulfonic acid, p-phenolsulfonic acid, o-cresolsulfonic acid, metanilic acid, sulfanilic acid, 4B-acid, diaminostilbenesulfonic acid, biphenylsulfonic acid, α-naphthalenesulfonic acid, β-naphthalenesulfonic acid, peri acid, Laurent's acid and phenyl-J-acid (7-anilino-4-hydroxy-2-naphthalenesulfonic acid). Several of them may be used in combination. Preferred are organic carboxylic acids such as formic acid, acetic acid, peracetic acid, thioacetic acid, oxalic acid, tartaric acid, propionic acid, butyric acid, succinic acid, valeric acid, caproic acid, caprylic acid, naphthenic acid, methyl mercaptopropionate, malonic acid, glutaric acid, adipic acid, cyclohexanecarboxylic acid, thiodipropionic acid, dithiodipropionic acid acetic acid, maleic acid, benzoic acid, phenylacetic acid, o-toluic acid, m-toluic acid, p-toluic acid, salicylic acid, 2-methoxybenzoic acid, 3-methoxybenzoic acid, benzoylbenzoic acid, phthalic acid, isophthalic acid, terephthalic acid, salicylic acid, benzilic acid, α-naphthalenecarboxylic acid, β-naphthalenecarboxylic acid, acetic anhydride, propionic anhydride, butyric anhydride, succinic anhydride, maleic anhydride, benzoic anhydride, phthalic anhydride, pyromellitic dianhydride, trimellitic anhydride and trifluoroacetic anhydride. More preferred are acid anhydrides such as acetic anhydride, propionic anhydride, butyric anhydride, succinic anhydride, maleic anhydride, benzoic anhydride, phthalic anhydride, pyromellitic dianhydride, trimellitic anhydride and trifluoroacetic anhydride. Acetic anhydride is most preferred. The amount of the acid or acid anhydride to be added is usually 0.001 to 10% by mass, and preferably 0.01 to 5% by mass relative to the total amount of the reaction solution. When the amount to be added is less than 0.001% by mass, polymer formation becomes pronounced, resulting in reduction in the yield of the reaction, and when the amount is more than 10% by mass, the yield may be significantly reduced.

Further, specific examples of the ammonium salt include ammonium chloride, ammonium bromide, ammonium iodide, ammonium formate, ammonium acetate, ammonium propionate, ammonium benzoate, ammonium sulfate, ammonium nitrate, ammonium carbonate, ammonium phosphate and ammonium hydroxide. Ammonium nitrate, ammonium sulfate and ammonium chloride are more preferred, and ammonium nitrate is most preferred.

The reaction is monitored by NMR, IR, liquid chromatograph or gas chromatograph and terminated in a state where the compound represented by formula (1) remains. In one embodiment, the reaction is terminated in a state where the compounds (B1), (B2) and (B3) exist at a desired ratio. In another embodiment, the reaction is terminated in a state where the amount of the compound represented by formula (1) is 0.05 to 20% by mass, more preferably 0.1 to 15% by mass, particularly preferably 0.5 to 10% by mass, and most preferably 0.5 to 4% by mass.

The compound represented by formula (1) thus obtained is subjected to column purification, thereby isolating the compound (B1), the compound (B2) and the compound (B3) respectively.

In the case of obtaining the compound represented by formula (2), the reaction is monitored by NMR, IR, liquid chromatograph or gas chromatograph and terminated in a state where epoxy rings have been completely converted into epithio rings.

The composition for optical materials can be obtained by mixing the compound represented by formula (1) obtained by the above-described reaction or the compound (B1), the compound (B2) and/or the compound (B3) obtained by isolation therefrom with the compound represented by formula (2).

[1,2,3,5,6-pentathiepane (c)]

The composition for optical materials of the present invention may contain 1,2,3,5,6-pentathiepane (c) according to need.

1,2,3,5,6-pentathiepane (c) is a compound represented by formula (c) below and has the effect of improving the refractive index of an optical material (resin) obtained from the composition for optical materials of the present invention.

The method for obtaining 1,2,3,5,6-pentathiepane (c) is not particularly limited. A commercially-available product may be used as 1,2,3,5,6-pentathiepane (c). Alternatively, 1,2,3,5,6-pentathiepane (c) may be collected and extracted from natural material such as crude oil, animals and plants or may be synthesized according to a publicly-known method.

Examples of synthesis methods include those described in: N. Takeda et al., Bull. Chem. Soc. Jpn., 68, 2757 (1995); F. Feher et al., Angew. Chem. Int. Ed., 7, 301 (1968); G. W. Kutney et al., Can. J. Chem, 58, 1233 (1980); etc.

When using 1,2,3,5,6-pentathiepane (c), the ratio thereof in the composition for optical materials is preferably 5 to 70% by mass, and more preferably 5 to 50% by mass relative to the total amount of the composition for optical materials. When the ratio is within the above-described range, a balance between the improvement of the refractive index and transparency of the optical material can be achieved.

[Polythiol (d)]

The composition for optical materials may contain a polythiol (d) according to need. The polythiol (d) is a thiol compound having at least two mercapto groups per one molecule. The polythiol (d) has the effect of improving the color tone of resin obtained from the composition for optical materials of the present invention at the time of heating.

The polythiol to be used in the present invention is not particularly limited, but in terms of being highly effective for the improvement of the color tone, preferred specific examples thereof include 1,2,6,7-tetramercapto-4-thiaheptane, methanedithiol, (sulfanylmethyldisulfanyl)methanethiol, bis(2-mercaptoethyl)sulfide, 2,5-bis(mercaptomethyl)-1,4-dithiane, 1,2-bis(2-mercaptoethylthio)-3-mercaptopropane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,3,3-tetrakis(mercaptomethylthio)propane, tetramercaptopentaerythritol, 1,3-bis(mercaptomethyl)benzene, 1,4-bis(mercaptomethyl)benzene and thiiranemethanethiol. Particularly preferred are bis(2-mercaptoethyl)sulfide, 1,2,6,7-tetramercapto-4-thiaheptane, 1,2-bis(2-mercaptoethylthio)-3-mercaptopropane and 1,3-bis(mercaptomethyl)benzene, and most preferred is 1,2,6,7-tetramercapto-4-thiaheptane. As these materials, a commercially-available product or a product obtained by synthesis according to a publicly-known method can be used. Further, two or more of these materials can be used in combination.

The ratio of the polythiol (d) in the composition for optical materials is preferably 0 to 25% by mass (e.g., 0.1 to 25% by mass), more preferably 0 to 20% by mass (e.g., 0.5 to 20% by mass), even more preferably 0 to 15% by mass (e.g., 0.5 to 15% by mass), and particularly preferably 0 to 12% by mass (e.g., 0.5 to 12% by mass) relative to the total amount of the composition for optical materials.

[Sulfur]

The composition for optical materials may contain sulfur according to need. Sulfur has the effect of improving the refractive index of the optical material (resin) obtained from the composition for optical materials of the present invention.

The sulfur to be used in the present invention may be in any form. Specific examples of the sulfur include finely-powdered sulfur, colloidal sulfur, precipitated sulfur, crystalline sulfur and sublimed sulfur, and from the viewpoint of the dissolution rate, finely-powdered sulfur having fine particles is preferred.

It is preferred that the particle size (diameter) of the sulfur to be used in the present invention is less than 10 mesh. When the particle size of the sulfur is more than 10 mesh, it is difficult to dissolve the sulfur completely. The particle size of the sulfur is more preferably less than 30 mesh, and most preferably less than 60 mesh.

The purity of the sulfur to be used in the present invention is preferably at least 98%, more preferably at least 99.0%, even more preferably at least 99.5%, and most preferably at least 99.9%. When the purity of the sulfur is at least 98%, the color tone of the obtained optical material is improved compared to the case of lower than 98%.

As the sulfur satisfying the above-described conditions, a commercially-available product can be easily obtained and suitably used.

In the composition for optical materials, the ratio of the sulfur is usually 0 to 40% by mass (e.g., 1 to 40% by mass), preferably 0 to 30% by mass (e.g., 5 to 30% by mass or 10 to 30% by mass), more preferably 0 to 25% by mass (e.g., 5 to 25% by mass), and particularly preferably 0 to 20% by mass (e.g., 5 to 20% by mass) relative to the total amount of the composition for optical materials.

When obtaining an optical material by polymerizing and curing the composition for optical materials of the present invention, it is preferred to add a polymerization catalyst. As the polymerization catalyst, amines, phosphines and onium salts may be used, but onium salts are particularly preferred. Among them, quaternary ammonium salts, quaternary phosphonium salts, tertiary sulfonium salts and secondary iodonium salts are preferred. Among them, quaternary ammonium salts and quaternary phosphonium salts, which have good compatibility with the composition for optical materials, are more preferred, and quaternary phosphonium salts are even more preferred. More preferred examples of the polymerization catalyst include quaternary ammonium salts such as tetra-n-butylammonium bromide, triethylbenzyl ammonium chloride, cetyldimethylbenzyl ammonium chloride and 1-n-dodecyl pyridinium chloride and quaternary phosphonium salts such as tetra-n-butylphosphonium bromide and tetraphenyl phosphonium bromide. Among them, tetra-n-butylammonium bromide, triethylbenzyl ammonium chloride and tetra-n-butylphosphonium bromide are even more preferred polymerization catalysts.

The amount of the polymerization catalyst to be added cannot be determined categorically because it varies depending on the components of the composition, the mixing ratio and the method for polymerization and curing, but the amount is usually 0.0001 to 10% by mass, preferably 0.001 to 5% by mass, more preferably 0.01 to 1% by mass, and most preferably 0.01 to 0.5% by mass relative to the total amount (100% by mass) of the composition for optical materials. When the amount of the polymerization catalyst to be added is more than 10% by mass, the composition may be rapidly polymerized. When the amount of the polymerization catalyst to be added is less than 0.0001% by mass, the composition for optical materials may be insufficiently cured, resulting in poor heat resistance.

Moreover, in the production of the optical material according to the production method of the present invention, it is surely possible to add additives such as an ultraviolet absorber, a blueing agent and a pigment to the composition for optical materials to further improve practicability of the optical material obtained.

Preferred examples of the ultraviolet absorber include benzotriazole-based compounds, and 2-(2-hydroxy-5-methylphenyl)-2H-benzotriazol, 5-chloro-2-(3,5-di-tert-butyl-2-hydroxyphenyl)-2H-benzotriazol, 2-(2-hydroxy-4-octylphenyl)-2H-benzotriazol, 2-(2-hydroxy-4-methoxyphenyl)-2H-benzotriazol, 2-(2-hydroxy-4-ethoxyphenyl)-2H-benzotriazol, 2-(2-hydroxy-4-butoxyphenyl)-2H-benzotriazol, 2-(2-hydroxy-4-octyloxyphenyl)-2H-benzotriazol and 2-(2-hydroxy-5-t-octylphenyl)-2H-benzotriazol are particularly preferred compounds.

The amount of each of the antioxidant and the ultraviolet absorber to be added is usually 0.01 to 5% by mass relative to the total amount (100% by mass) of the composition for optical materials.

When polymerizing and curing the composition for optical materials, for the purpose of extension of the pot life, dispersion of heat generated by polymerization, etc., a polymerization modifier may be added according to need. Examples of the polymerization modifier include halides of groups 13 to 16 of the long form of the periodic table. Among them, halides of silicon, germanium, tin and antimony are preferred, and chlorides of germanium, tin and antimony, which have an alkyl group, are more preferred. Further, dibutyltin dichloride, butyltin trichloride, dioctyltin dichloride, octyltin trichloride, dibutyldichlorogermanium, butyltrichlorogermanium, diphenyldichlorogermanium, phenyltrichlorogermanium and triphenylantimony dichloride are even more preferred, and dibutyltin dichloride is the most preferred compound. These polymerization modifiers may be used solely, or two or more of them may be used in combination.

The amount of the polymerization modifier to be added is 0.0001 to 5.0% by mass, preferably 0.0005 to 3.0% by mass, and more preferably 0.001 to 2.0% by mass relative to the total amount (100% by mass) of the composition for optical materials. When the amount of the polymerization modifier to be added is less than 0.0001% by mass, sufficient pot life cannot be ensured in the obtained optical material, and when the amount of the polymerization modifier to be added is more than 2.0% by mass, the composition for optical materials may not be sufficiently cured, and the heat resistance of the obtained optical material may be reduced.

The composition for optical materials thus obtained is injected into a mold or the like and polymerized to obtain an optical material.

At the time of cast-molding the composition for optical materials of the present invention, it is preferred to filter and remove impurities using, for example, a filter having a pore diameter of about 0.1 to 5 μm in terms of improving the quality of the optical material of the present invention.

The composition for optical materials of the present invention is usually polymerized as described below. Specifically, the curing time is usually 1 to 100 hours, and the curing temperature is usually −10° C. to 140° C. The polymerization is conducted by carrying out a step of retaining the composition at a predetermined polymerization temperature for a predetermined amount of time, a step of increasing the temperature at a rate of 0.1° C. to 100° C./h and a step of decreasing the temperature at a rate of 0.1° C. to 100° C./h, or a combination of these steps.

Further, it is preferred to anneal the obtained optical material at a temperature of 50 to 150° C. for about 10 minutes to 5 hours after curing is completed in terms of eliminating distortion of the optical material of the present invention. Moreover, the obtained optical material may be subjected to a surface treatment such as dyeing, hard coating, impact-resistant coating, antireflection treatment and imparting antifog properties according to need.

The optical material of the present invention can be suitably used as an optical lens.

EXAMPLES

Hereinafter, the present invention will be specifically described by way of working examples and comparative examples. However, the present invention is not limited to the below-described working examples. Note that optical materials obtained according to the below-described methods of working examples and comparative examples were evaluated according to the below-described methods.

1. Method for Evaluating Mold Releasability 10 lenses having a lens power of +12D were prepared according to the method described in the Examples below. When the lenses were released from molds, the case where no lens was broken was rated as "A", the case where 1 lens was broken was rated as "B", and the case where 2 or more lenses were broken was rated as "C". A and B are regarded as acceptable. A and B are preferred, and A is particularly preferred.

2. Method for Evaluating Peeling Traces 10 lenses having a lens power of −15D were prepared according to the method described in the Examples below. After released from molds, the lenses were annealed at 120° C. for 30 minutes, and then surface conditions thereof were visually observed. Regarding the 10 lenses prepared, the case where no peeling trace was generated in the lenses was rated as "A", the case where 1 lens had peeling traces was rated as "B", and the case where 2 or more lenses had peeling traces was rated as "C". A and B are regarded as acceptable. A and B are preferred, and A is particularly preferred.

3. Method for Evaluating Transparency

According to the methods described in the Examples and Comparative Examples below, 10 lenses were prepared, and the lenses were observed under a fluorescent light in a dark room. The case where no white turbidity was observed in the 10 lenses was rated as "A". The case where white turbidity was not observed in 7 to 9 lenses was rated as "B". The case where white turbidity was not observed in 6 lenses or less was rated as "C". A and B are regarded as acceptable.

4. Method for Evaluating Striae

According to the methods described in the Examples and Comparative Examples below, 10 lenses were prepared, and the lenses were visually observed according to the schlieren method. The case where no stria was observed in the 10 lenses was rated as "A". The case where striae were not observed in 7 to 9 lenses was rated as "B". The case where striae were not observed in 6 lenses or less was rated as "C". A and B are regarded as acceptable.

Example 1

To 20.1 g (0.047 mol) of tetrakis(β-epoxypropylthiomethyl)methane, 100 mL of toluene, 100 mL of methanol, 1.24 g (0.012 mol) of acetic anhydride and 30.5 g (0.40 mol) of thiourea were added, and the mixture was stirred at 20° C. for 6 hours. After that, 400 mL of toluene and 400 mL of 5% sulfuric acid were added thereto, the toluene layer was washed with water three times, and the solvent was distilled away, thereby obtaining 16.8 g of a crude product of tetrakis(β-epithiopropylthiomethyl)methane. The crude product was further subjected to silica gel column purification, thereby obtaining 11.2 g of a compound (1) (hereinafter referred to as "the compound b"). It was subjected to the NMR measurement, and it was confirmed that a compound in which $X_1=X_2=O$, a compound in which $X_1=O$ and $X_2=S$ and a compound in which $X_1=X_2=S$ were contained therein at a mass ratio of 40:30:30.

The compound (1) used in the below-described experiments was synthesized according to this method.

$X_1=X_2=O$ (Episulfide compound (B1))
$^1$H-NMR (CDCl$_3$): 2.54 ppm (1H), 2.34 ppm, 2.09 ppm (2H), 2.81 ppm (3H), 2.61 ppm, 2.36 ppm (6H), 2.88 ppm, 2.63 ppm (2H), 2.67 ppm, 2.43 ppm (6H), 2.30 ppm (8H)
$^{13}$C-NMR (CDCl$_3$): 32.6 ppm (1C), 26.4 ppm (1C), 53.8 ppm (3C), 46.8 ppm (3C), 44.8 ppm (1C), 41.5 ppm (3C), 37.5 ppm (1C), 37.6 ppm (3C), 38.9 ppm (1C)

$X_1=O$ and $X_2=S$ (Episulfide compound (B2))
$^1$H-NMR (CDCl$_3$): 2.54 ppm (2H), 2.34 ppm, 2.09 ppm (4H), 2.81 ppm (2H), 2.61 ppm, 2.36 ppm (4H), 2.88 ppm, 2.63 ppm (4H), 2.67 ppm, 2.43 ppm (4H), 2.30 ppm (8H)
$^{13}$C-NMR (CDCl$_3$): 32.6 ppm (2C), 26.4 ppm (2C), 53.8 ppm (2C), 46.8 ppm (2C), 44.8 ppm (2C), 41.5 ppm (2C), 37.5 ppm (2C), 37.6 ppm (2C), 38.9 ppm (1C)

$X_1=X_2=S$ (Episulfide compound (B3))
$^1$H-NMR (CDCl$_3$): 2.54 ppm (4H), 2.34 ppm, 2.09 ppm (8H), 2.88 ppm, 2.63 ppm (8H), 2.30 ppm (8H)
$^{13}$C-NMR (CDCl$_3$): 32.6 ppm (3C), 26.4 ppm (3C), 53.8 ppm (1C), 46.8 ppm (1C), 44.8 ppm (3C), 41.5 ppm (1C), 37.5 ppm (3C), 37.6 ppm (1C), 38.9 ppm (1C)

Examples 2-7 and Reference Example 1

Tetrakis(β-epithiopropylthiomethyl)methane that is the episulfide compound represented by formula (2) (hereinafter referred to as "the compound a") was mixed with the compound represented by formula (1) obtained in Example 1 (hereinafter referred to as "the compound b") to prepare a composition in which the ratio between the compound a and the compound b was as shown in Table 1. To 55 parts by mass of the obtained composition, 35 parts by mass of 1,2,3,5,6-pentathiepane (c), 10 parts by mass of 1,2,6,7-tetramercapto-4-thiaheptane and 0.05 part by mass of tetra-n-butylphosphonium bromide as a polymerization catalyst were added, and then the mixture was sufficiently mixed to be homogeneous. Subsequently, the obtained mixture was subjected to the deaeration treatment at a vacuum degree of 1.3 kPa and injected into a mold composed of two glass plates and a tape. It was heated at 30° C. for 10 hours, then the temperature was elevated to 100° C. at a constant rate over 10 hours, and finally, it was heated at 100° C. for 1 hour to be polymerized and cured. After cooling, the obtained product was released from the mold and annealed at 120° C. for 30 minutes to obtain a molded plate (12D or −15D). Mold releasability, peeling traces, transparency and striae of the obtained optical material were evaluated. The evaluation results are shown in Table 1.

Comparative Example 1

A molded plate was obtained in a manner similar to that in Example 2, except that the compound a was used instead of the composition obtained by mixing the compound a and the compound b. The evaluation results are shown in Table 1.

TABLE 1

| Examples | Addition amount of Compound a (% by mass) | Addition amount of Compound b (% by mass) | Compound ratio in Compound b (% by mass) $X_1 = X_2 = O$ | Compound ratio in Compound b (% by mass) $X_1 = O, X_2 = S$ | Compound ratio in Compound b (% by mass) $X_1 = X_2 = S$ | Mold releasability | Peeling traces | Transparency | Striae |
|---|---|---|---|---|---|---|---|---|---|
| Example 2 | 99.999 | 0.001 | 40 | 30 | 30 | A | A | B | B |
| Example 3 | 99.995 | 0.005 | 40 | 30 | 30 | A | A | B | B |
| Example 4 | 99.99 | 0.01 | 40 | 30 | 30 | A | A | A | A |
| Example 5 | 99.0 | 1.0 | 40 | 30 | 30 | A | A | A | A |
| Example 6 | 97.0 | 3.0 | 40 | 30 | 30 | B | A | A | A |
| Example 7 | 95.0 | 5.0 | 40 | 30 | 30 | B | B | A | A |
| Comparative Example 1 | 100 | Not added | — | — | — | A | A | C | C |
| Reference Example 1 | 93.0 | 7.0 | 40 | 30 | 30 | C | C | A | A |

Examples 8-13 and Comparative Example 2

Tetrakis(β-epithiopropylthiomethyl)methane that is the episulfide compound represented by formula (2) (hereinafter referred to as "the compound a") was mixed with the compound represented by formula (1) obtained in Example 1 (hereinafter referred to as "the compound b") to prepare a composition in which the ratio between the compound a and the compound b was as shown in Table 2. To 60 parts by mass of the obtained composition, 25 parts by mass of 1,2,3,5,6-pentathiepane (c), 5 parts by mass of 1,2,6,7-tetramercapto-4-thiaheptane, 10 parts by mass of sulfur and 0.05 part by mass of tetra-n-butylphosphonium bromide as a polymerization catalyst were added, and then the mixture was sufficiently mixed to be homogeneous. Subsequently, the obtained mixture was subjected to the deaeration treatment at a vacuum degree of 1.3 kPa and injected into a mold composed of two glass plates and a tape. It was heated at 30° C. for 10 hours, then the temperature was elevated to 100° C. at a constant rate over 10 hours, and finally, it was heated at 100° C. for 1 hour to be polymerized and cured. After cooling, the obtained product was released from the mold and annealed at 120° C. for 30 minutes to obtain a molded plate (12D or −15D). Mold releasability, peeling traces, transparency and striae of the obtained optical material were evaluated. The evaluation results are shown in Table 2.

TABLE 2

| Examples | Addition amount of Compound a (% by mass) | Addition amount of Compound b (% by mass) | Compound ratio in Compound b (% by mass) $X_1 = X_2 = O$ | Compound ratio in Compound b (% by mass) $X_1 = O, X_2 = S$ | Compound ratio in Compound b (% by mass) $X_1 = X_2 = S$ | Mold releasability | Peeling traces | Transparency | Striae |
|---|---|---|---|---|---|---|---|---|---|
| Example 8 | 99.999 | 0.001 | 40 | 30 | 30 | A | A | B | B |
| Example 9 | 99.995 | 0.005 | 40 | 30 | 30 | A | A | B | B |
| Example 10 | 99.99 | 0.01 | 40 | 30 | 30 | A | A | A | A |
| Example 11 | 99.0 | 1.0 | 40 | 30 | 30 | A | A | A | A |
| Example 12 | 97.0 | 3.0 | 40 | 30 | 30 | B | A | A | A |
| Example 13 | 95.0 | 5.0 | 40 | 30 | 30 | B | B | A | A |
| Comparative Example 2 | 100 | Not added | — | — | — | A | A | C | C |

As shown in Table 1 and Table 2 above, it is confirmed that in the case of the compositions of the Examples containing the episulfide compound represented by formula (1) (compound b) and the episulfide compound represented by formula (2) (compound a), mold release failure and peeling defects at the time of polymerization and curing are suppressed and high-quality optical materials having high transparency and low-level striae are obtained.

The invention claimed is:

1. An episulfide compound represented by formula (1):

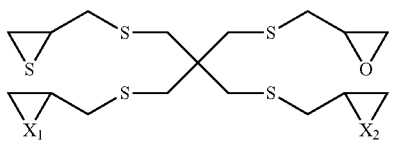

(1)

wherein $X_1$ and $X_2$ represent O or S, provided that both $X_1$ and $X_2$ are O or that $X_1$ is O and $X_2$ is S.

2. A composition for optical materials, which contains an episulfide compound represented by formula (1):

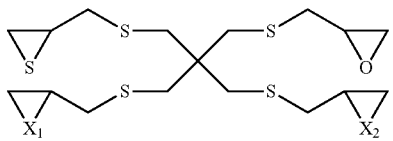

(1)

wherein $X_1$ and $X_2$ represent O or S, and an episulfide compound represented by formula (2):

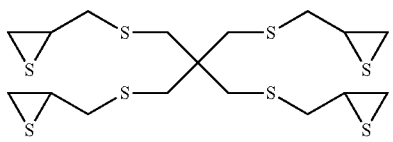

(2)

wherein the content of the episulfide compound represented by formula (1) is 0.001 to 5.0% by mass.

3. The composition for optical materials according to claim 2, wherein the content of the episulfide compound represented by formula (2) is 40 to 99.999% by mass.

4. The composition for optical materials according to claim 2, wherein in the episulfide compound represented by formula (1) contained in the composition for optical materials, the ratio of the total of an episulfide compound (B1) in which both $X_1$ and $X_2$ are O in formula (1) and an episulfide compound (B2) in which $X_1$ is O and $X_2$ is S in formula (1) is 50% by mass or more.

5. The composition for optical materials according to claim 2, which further contains 1,2,3,5,6-pentathiepane.

6. The composition for optical materials according to claim 2, which further contains a polythiol.

7. The composition for optical materials according to claim 2, which further contains sulfur.

8. A method for producing an optical material, which includes adding a polymerization catalyst to the composition for optical materials according to claim 2 in an amount of 0.0001 to 10% by mass relative to the total amount of the composition for optical materials, followed by polymerization and curing.

9. An optical material obtained by the method according to claim 8.

10. An optical lens made of the optical material according to claim 9.

11. A method for producing the composition for optical materials according to claim 2, which includes:

reacting an epoxy compound represented by formula (3):

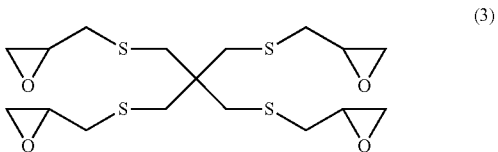

(3)

with thiourea and optionally adding the episulfide compound represented by formula (2) thereto to obtain a mixture of the episulfide compound represented by formula (1) and the episulfide compound represented by formula (2).

12. A method for producing the composition for optical materials according to claim 5, which includes:

reacting an epoxy compound represented by formula (3):

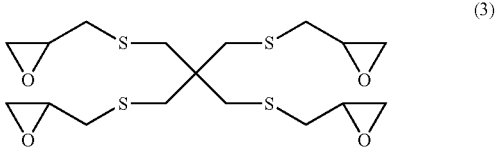 [SMILES: C(SCC(CSCC1CS1)(CSCC1CS1)CSCC1CS1)C1CS1]

(3)

with thiourea and optionally adding the episulfide compound represented by formula (2) thereto to obtain a mixture of the episulfide compound represented by formula (1) and the episulfide compound represented by formula (2); and mixing the mixture with 1,2,3,5,6-pentathiepane.

13. A method for producing the composition for optical materials according to claim 6, which includes:

reacting an epoxy compound represented by formula (3):

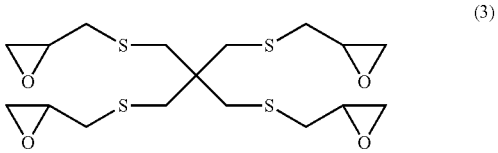

(3)

with thiourea and optionally adding the episulfide compound represented by formula (2) thereto to obtain a mixture of the episulfide compound represented by formula (1) and the episulfide compound represented by formula (2); and mixing the mixture with 1,2,3,5,6-pentathiepane and the polythiol.

14. A method for producing the composition for optical materials according to claim 7, which includes:

reacting an epoxy compound represented by formula (3):

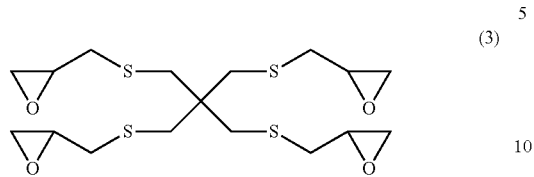

(3)

with thiourea and optionally adding the episulfide compound represented by formula (2) thereto to obtain a mixture of the episulfide compound represented by formula (1) and the episulfide compound represented by formula (2); and mixing the mixture, 1,2,3,5,6-pentathiepane, the polythiol and sulfur.

* * * * *